United States Patent

Behl et al.

[11] Patent Number: 5,451,310
[45] Date of Patent: Sep. 19, 1995

[54] SOLID STATE ELECTROCHEMICAL CELL OXYGEN SENSOR

[75] Inventors: Wishvender K. Behl, Ocean; Edward J. Plichta, Howell, both of N.J.

[73] Assignee: The United States of America as represented by the Secretary of the Army, Washington, D.C.

[21] Appl. No.: 209,511

[22] Filed: Feb. 21, 1994

[51] Int. Cl.$^6$ ............................................. G01N 27/409
[52] U.S. Cl. .................................... 204/426; 204/424
[58] Field of Search ................... 204/153.18, 421–429; 429/30, 33, 191, 193

[56] References Cited

U.S. PATENT DOCUMENTS

| | | | |
|---|---|---|---|
| 3,400,054 | 9/1968 | Ruka et al. | 204/427 |
| 3,506,490 | 4/1970 | Buzzelli | 429/191 |
| 3,506,491 | 4/1970 | Buzzelli | 429/191 |
| 4,042,482 | 8/1977 | Shannon et al. | 429/191 |
| 4,072,803 | 2/1978 | Schneider | 429/191 |
| 4,117,103 | 9/1978 | Hong | 429/193 |
| 4,172,882 | 10/1979 | Hong | 429/193 |
| 5,154,990 | 10/1992 | Plichta et al. | 429/191 |
| 5,273,846 | 12/1993 | Plichta et al. | 429/193 |
| 5,273,847 | 12/1993 | Plichta et al. | 429/218 |
| 5,278,004 | 1/1994 | Plichta et al. | 429/193 |
| 5,312,623 | 5/1994 | Plichta et al. | 429/193 |

*Primary Examiner*—T. Tung
*Attorney, Agent, or Firm*—Michael Zelenka; Roy E. Gordon

[57] ABSTRACT

A solid state electrochemical cell is provided including lithium-aluminum alloy as the anode, a solid solution of lithium germanium oxide ($Li_4GeO_4$) and lithium vanadium oxide ($Li_3VO_4$) as the electrolyte, and a platinum disk as the cathode. The cell is particularly suitable for use as an oxygen sensor to measure the partial pressure of oxygen gas at about 300° C. in a mixture of gases.

1 Claim, No Drawings

SOLID STATE ELECTROCHEMICAL CELL OXYGEN SENSOR

GOVERNMENT INTEREST

The invention described herein may be manufactured, used, and licensed by or for the Government for governmental purposes without the payment to us of any royalties thereon.

FIELD OF INVENTION

The invention relates in general to solid state electrochemical cells and in particular to solid state electrochemical cells that can be used as oxygen sensors to measure the partial pressure of oxygen gas at a temperature of about 300° C. in a mixture of gases.

BACKGROUND OF THE INVENTION

Oxygen sensors are needed for measuring the partial pressure of oxygen gas at high temperatures in mixtures of oxygen with inert gases such as argon, nitrogen, etc in flowing streams. Heretofore, the oxygen gauges have been based upon solid state electrochemical cells using calcia or yttria stabilized zirconia as the solid electrolyte. These cells, however, can only be operated at temperatures above 800° C.

SUMMARY OF THE INVENTION

The general object of this invention is to provide an all solid state electrochemical cell that can be used as an oxygen sensor to measure the partial pressure of oxygen in a mixture of gases. A more specific object of the invention is to provide an all solid state electrochemical cell that can be used as an oxygen sensor at lower temperatures than the electrochemical cells using calcia or yttria stabilized zirconia as the solid electrolyte.

It has now been found that the aforementioned objects can be attained by using a lithium ion conducting solid material that is stable in the presence of oxygen as the electrolyte in an all solid state electrochemical cell that can be operated at a temperature of about 300° C.

The preferred solid state electrochemical cell includes a lithium-aluminum alloy as the anode, a solid solution of lithium germanium oxide ($Li_4GeO_4$) and lithium vanadium oxide ($Li_3VO_4$) having the general formula $Li_{3+x}Ge_xV_{1-x}O_4$, where $0.2 < X < 0.8$ as the lithium ion conducting solid electrolyte and a platinum disk as the cathode. A solid solution having the composition, $Li_{3.6}Ge_{0.6}V_{0.4}O_4$, where $x = 0.6$ is prepared by pressing a 2.3 cm diameter pellet of a mixture of 1.33 gms of lithium carbonate, 0.628 gm of germanium oxide and 0.364 gm of vanadium pentoxide to a pressure of about 6,800 kg and firing in a gold crucible. The pellet is fired at 600° C. in air for two hours to evolve carbon dioxide followed by heating to 900° C. for 20 hours. The fired pellet is then quenched in air to room temperature and ground to a fine powder and stored in an argon filled dry box having a moisture content of less than 0.5 ppm.

DESCRIPTION OF THE PREFERRED EMBODIMENT

An all solid state electrochemical cell is fabricated by placing a 13 mm diameter × 1 mm thick pressed pellet of the solid electrolyte that is sintered for 4 hours at 1,000° C. onto a 13 mm diameter platinum disk including a 13 mm diameter pressed pellet of lithium-aluminum alloy placed on top of the solid electrolyte pellet. The whole cell stack is then sandwiched between two molybdenum plates, that act as the negative and positive terminals of the cell, in a spring loaded cell assembly. The cell assembly is then placed in a closed bottom pyrex glass vessel. The top end of the glass vessel is closed with a threaded Teflon stopper that is fitted with feedthrough connections to provide electrical connections to the negative and positive terminal of the cell and "swagelok" fittings to insert the thermocouple and gas inlet and outlet tubes. The glass container is placed inside a cylindrical furnace and heated to 300° C.

The all solid state cell can be represented as:

$$Li\text{-}Al/Li_{3.6}Ge_{0.6}V_{0.4}O_4/O_2, Pt \qquad \text{I}$$

The electrode reactions at the left hand electrode may be written as:

$$2\ Li\text{-}Al \rightleftharpoons 2\ Li^+ + 2\ Al + 2\ e \qquad (1)$$

The lithium ions produced at the left hand electrode are then transported through the lithium ion conducting solid electrolyte and react with oxygen at the right hand electrode to form lithium oxide according to the reaction, $$2\ Li^+ + \tfrac{1}{2}\ O_2 + 2e \rightleftharpoons Li_2O \qquad (2)$$

so that the net cell reaction is given by:

$$2\ Li\text{-}Al + \tfrac{1}{2}\ O_2 \rightleftharpoons Li_2O + 2\ Al \qquad (3)$$

The emf of the above cell is given by:

$$E = \frac{-\Delta G_{Li_2O}}{2F} + \frac{2.303 RT}{2F} \log a_{Li}^2 (P_{O_2})^{\tfrac{1}{2}} \qquad (4)$$

$$E = \frac{-\Delta G_{Li_2O}}{2F} + \frac{2.303 RT}{2F} \log a_{Li} + \frac{2.303 RT}{4F} \log P_{O_2} \qquad (5)$$

where $G_{Li_2O}$ is the free energy of formation of lithium oxide, $a_{Li}$ is the activity of the lithium metal in the lithium-aluminum alloy, T is the temperature in degrees Kelvin, R is the gas constant and F is the Faraday constant. The free energy of formation of lithium oxide is known to be $-125730$ cals./mole at 300° C. so that the first term in Equation 5 is calculated to be 2.7259V. From the literature, the value of the 2nd term in Equation 2 is known to be 0.3249V at 300° C. Thus, Equation 2 may be rewritten as:

$$E = 2.7259 - 0.3249 + \frac{2.303\ RT}{4F} \log P_{O_2} \qquad (6)$$

$$E = 2.401 + \frac{2.303\ RT}{4F} \log P_{O_2} \qquad (7)$$

Thus, the emf of cell I is directly related to the partial pressure of oxygen. If the emf of cell I is measured in an atmosphere of pure oxygen, the partial pressure of oxygen is unity and the 2nd term in Equation 7 is zero and the emf of the cell will be equal to 2.401V at 300° C. In pure argon atmosphere, the emf of the cell I is about 1.64V and as soon as some oxygen is introduced, the emf of cell I increases to about 2.2V to 2.4V depending upon the partial pressure of oxygen in the mixture. Thus, cell I can be used as a sensor for oxygen gas in mixtures of oxygen with argon or other inert gases. The cell can also be calibrated and then used to monitor the partial pressure of oxygen in gas mixtures with inert gases.

We wish it to be understood that we do not desire to be limited to the exact details of construction shown and described for obvious modification will occur to a person skilled in the art.

In lieu of LiAl as the anode, one can use lithium metal, other lithium metal alloys and lithium intercalated compounds such as LiSi, LiB, $LiC_6$, $LiTiS_2$, $LiVSe_2$, lithiated graphite, and lithiated petroleum coke.

What is claimed is:

1. A solid state electrochemical cell used as an oxygen sensor to measure the partial pressure of oxygen gas at a temperature of about 300° C. in a mixture of gases, said solid state electrochemical cell including a lithium-aluminum alloy as the anode, a solid solution of lithium germanium oxide and lithium vanadium oxide having the general formula $Li_{3+x}Ge_xV_{1-x}O_4$, where $0.2 < X < 0.8$ as the lithium ion conducting solid electrolyte and a platinum disk as the cathode, the solid state electrochemical cell being made by placing a pressed pellet of the solid electrolyte that is sintered for 4 hours at 1000° C. onto a 13 mm diameter platinum disk and a 13 mm diameter pressed pellet of lithium-aluminum alloy atop the solid electrolyte pellet to form a cell stack, the cell stack being sandwiched between two molybdenum plates that act as the negative and positive terminals of the cell.

* * * * *